United States Patent [19]

Braginetz et al.

[11] Patent Number: 4,932,945
[45] Date of Patent: Jun. 12, 1990

[54] DISPOSABLE SHIELDED CATHETER-CANNULA INSERTION NEEDLE

[76] Inventors: Paul A. Braginetz, 214 Oak Ridge Cir.; Mark R. Leadbetter, 1926 Spring Hill Rd.; Joseph A. Peduto, Rte. 5, all of Staunton, Va. 24401

[21] Appl. No.: 286,249
[22] Filed: Dec. 19, 1988
[51] Int. Cl.$^5$ .............................................. A61M 5/32
[52] U.S. Cl. ...................................... 604/195; 604/198
[58] Field of Search ............... 604/195, 198, 187, 192, 604/158, 162, 164, 263, 220

[56] References Cited

U.S. PATENT DOCUMENTS

| | | | |
|---|---|---|---|
| 1,838,039 | 12/1931 | Montuori | 604/220 |
| 4,710,170 | 12/1987 | Haber et al. | 604/110 |
| 4,808,169 | 2/1989 | Haber et al. | 604/195 |

Primary Examiner—John D. Yasko
Attorney, Agent, or Firm—Brady, O'Boyle & Gates

[57] ABSTRACT

A disposable, shielded catheter-cannula insertion needle wherein a catheter-cannula assembly is detachably connected to the distal end of a housing having a piston assembly slidably mounted therein. The insertion needle extends through the catheter-cannula and is connected to the piston assembly. A stem, including a cap, is detachably connected to the housing to provide a cover for the catheter-cannula and connectable to the piston assembly for drawing the contaminated insertion needle into a shielded position within the housing. The catheter-cannula assembly includes a self-sealing bushing for closing the flow-through passage in the catheter-cannula when the insertion needle has been removed therefrom.

10 Claims, 1 Drawing Sheet

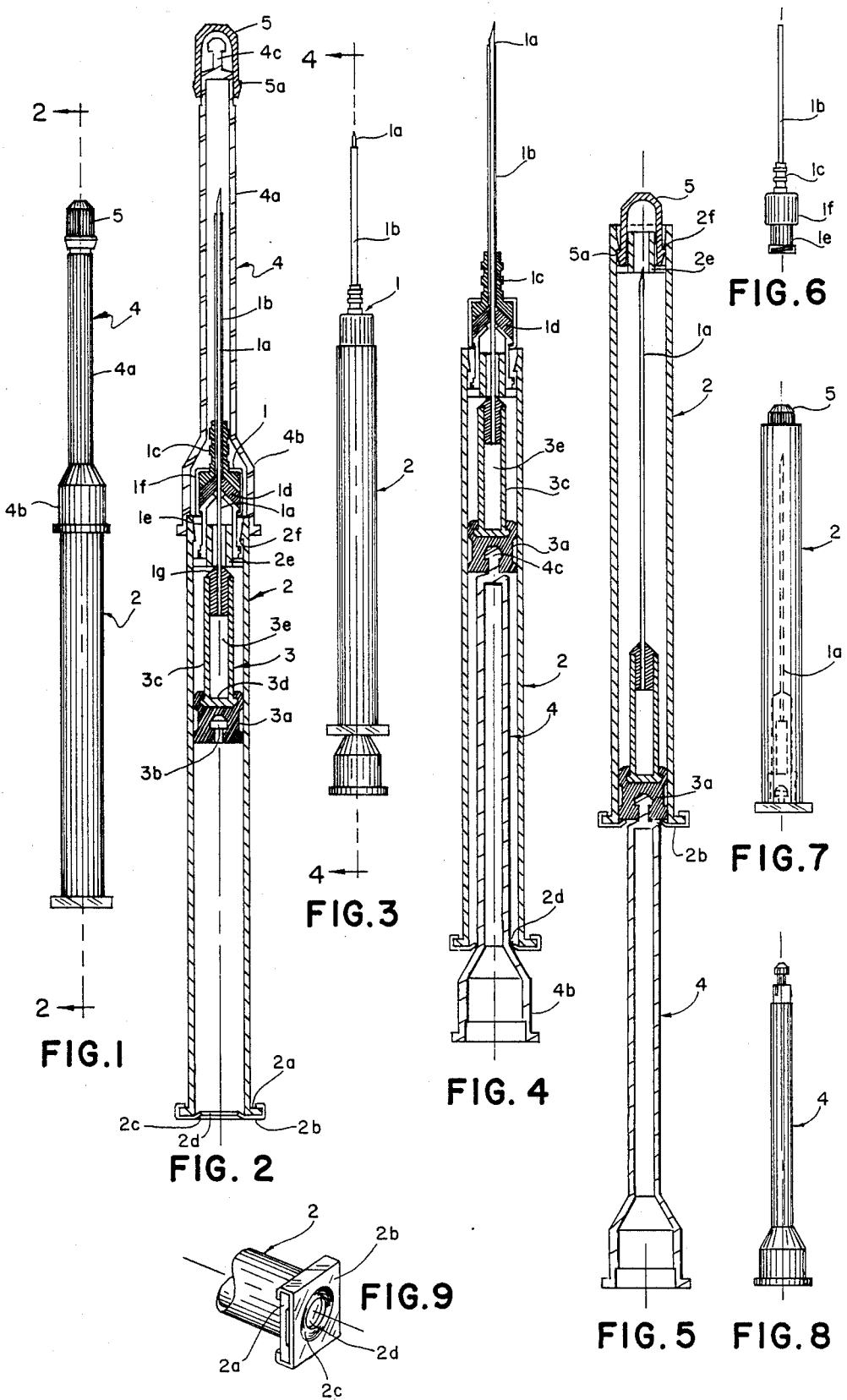

DISPOSABLE SHIELDED CATHETER-CANNULA INSERTION NEEDLE

BACKGROUND OF THE INVENTION

Short, flexible catheter-cannulas inserted into a blood vessel are employed to a great extent for sampling blood and the intravenous administration of drugs, fluid and blood. They have the advantage over steel needles because they do not easily cause vessel and tissue injuries and haematoma formation when the patient moves. The catheter-cannula is inserted into the blood vessel by a needle slidably mounted within the catheter-cannula, the needle being withdrawn from the catheter-cannula after its insertion into the blood vessel.

Medical personnel have to exercise the utmost of care when using catheter-cannula insertion needles so as not to be accidentally punctured by a contaminated needle resulting in possible exposure to infectious diseases, such as, acquired immune deficiency syndrome (AIDS) or serum hepatitis when inserting a catheter-cannula into the blood vessel of a patient.

In order to provide medical personnel with a safeguard against infectious diseases when manipulating a catheter-cannula insertion needle, the disposable shielded catheter-cannula insertion needle of the present invention has been devised, which comprises, essentially, a catheter-cannula assembly detachably connected to the distal end of a cylindrical housing. A piston assembly is slidably mounted within the housing with the insertion needle being connected to the piston assembly and extending coaxially within the catheter-cannula with the piercing end of the needle protruding from the distal end of the catheter-cannula assembly. A stem, including a cap, is detachably connected to the distal end of the cylindrical housing to provide a cover for the catheter-cannula and insertion needle assembly before use, the stem being insertable into the proximate end of the cylindrical housing and detachably connectable to the piston assembly for drawing the contaminated insertion needle into the cylindrical housing after the catheter-cannula has been inserted into the patient's blood vessel. The cap is connectable to the distal end of the cylindrical housing to completely enclose the contaminated insertion needle within the cylindrical housing, whereby the shielded contaminated insertion needle can be discarded.

BRIEF DESCRIPTION OF THE DRAWINGS

FIG. 1 is a side elevational view of the disposable shielded catheter-cannula insertion needle of the present invention as shipped and before use;

FIG. 2 is an enlarged sectional view taken along line 2—2 of FIG. 1;

FIG. 3 is a side elevational view of the disposable, shielded catheter-cannula insertion needle with the stem and cap removed from the cover position preparatory to insertion of the needle and catheter-cannula into the patient's blood vessel;

FIG. 4 is an enlarged sectional view taken along line 4—4 of FIG. 3;

FIG. 5 is a sectional side elevational view showing the contaminated insertion needle withdrawn into the shielded position within the cylindrical housing:

FIG. 6 is a side elevational view of the catheter-cannula detached from the cylindrical housing;

FIG. 7 is a side elevational view of the cylindrical housing and cap enclosing the contaminated insertion needle; and FIG. 8 is a side elevational view of the stem detached from the piston assembly within the cylindrical housing.

FIG. 9 is a fragmentary perspective view of the proximate end of the housing having a retainer spring clip mounted thereon.

DESCRIPTION OF THE PREFERRED EMBODIMENT

Referring to the drawings and more particularly to FIGS. 1 and 2, the disposable shielded catheter-cannula insertion needle of the present invention comprises, a catheter-cannula and insertion needle assembly 1 detachably connected to the distal end of a cylindrical housing 2. A piston assembly 3 is slidably mounted within the cylindrical housing 2 and is connected to the proximate end of the insertion needle 1a. A stem 4, including a cap 5, is detachably connected to the distal end of the cylindrical housing 2 to provide a cover for the catheter-cannula and insertion needle assembly 1 before use.

The catheter-cannula and insertion needle assembly 1 comprises the insertion needle 1a slidably mounted within the catheter-cannula 1b and having its distal end protruding outwardly from the distal end of the catheter-cannula 1b. The proximate end of the catheter-cannula 1b is integrally connected to a base 1c. A self-sealing resilient bushing 1d is mounted between the base 1c of the catheter-cannula 1b and a Luer-lock member 1e, the base 1c, bushing 1d and Luer-lock member 1e being held in the assembled position by a roll formed sleeve 1f.

The proximate end portion of the insertion needle 1a extends downwardly through the catheter-cannula base 1c, the bushing 1d and Luer-lock member 1e and is provided with a base member 1g fixedly connected to the piston assembly 3.

The cylindrical housing 2 is transparent and includes a flange portion 2a on its proximate end upon which a retainer spring clip 2b is mounted. The spring clip 2b includes a flexible circular lip portion 2c surrounding an opening 2d communicating with the interior of the cylindrical housing 2. The distal end portion of the cylindrical housing 2 is provided with a boss or nipple 2e upon which the Luer-lock member 1e is slip-fit, and an inwardly extending shoulder 2f is provided on the inner wall surface of the distal end of the housing 2 for cooperation with an outwardly extending shoulder portion 5a provided on the cap 5, to be described more fully hereinafter.

The piston assembly 3 comprises a piston 3a having a recess or entrant portion 3b on one face thereof. A transparent tubular member 3c, having an end wall 3d, is connected to the opposite face of the piston 3a, the opposite end of the tubular member 3c being closed by the insertion needle base 1g, to thereby provide a chamber 3e within the tubular member 3c communicating with the interior of the insertion needle 1a.

The stem 4 comprises an elongated hollow member 4a having an enlarged open end 4b adapted to be slip-fit onto the distal end of the cylindrical housing 2 over the catheter-cannula and insertion needle assembly 1. The opposite end of the stem 4 is closed and provided with a projection 4c correspondingly configured to the piston entrant portion 3b.

In the operation of the disposable, shielded catheter-cannula insertion needle of the present invention, the stem 4 and associated cap 5 are removed from the catheter-cannula and insertion needle assembly 1, as shown in FIGS. 3 and 4, and the stem 4 is inserted into the cylindrical housing 2 through the spring clip opening 2d. The projection 4c on the closed end of the stem 4 is inserted into the entrant portion 3b of the piston 3a, to thereby connect the stem 4 to the piston 3a. The medical person then inserts the needle 1a and catheter-cannula 1b into the patient's blood vessel. If the assembly has been properly inserted, the patient's blood will flow through the needle 1a into the chamber 3e. Since the cylindrical housing 2 and tubular member 3c are transparent, the flow of blood into the chamber 3e will be readily visible. The contaminated needle 1a is then drawn to the shielded position within the cylindrical housing 2, as shown in FIG. 5, by pulling the stem 4 outwardly through the open end of the housing 2. The spring clip 2b prevents removal of the piston 3a and associated contaminated needle 1a from the cylindrical housing 2.

During the sliding of the insertion needle 1a into the cylindrical housing 2, the self-sealing bushing 1d engages the outer wall surface of the needle until the end of the needle passes therethrough: at which time, the bushing 1d closes upon itself, to thereby seal the proximate end of the catheter-cannula 1b, whereby the flow of blood therethrough is prevented. The catheter-cannula 1b and associated Luer-lock member 1e are then removed from the housing nipple 2e, as shown in FIG. 6, and are connectable to a conventional syringe or intravenous fluid supply system, it being understood by those skilled in the art that the syringe or intravenous fluid supply system will include a needle insertable through the self-sealing bushing 1d to thereby re-open the catheter-cannula 1b to the flow of fluid.

To complete the operation of the device of the present invention, the cap 5 is slipped onto the housing nipple 2e and locked thereon by the interengagement of the shoulders 2f and 5a; the stem 4 is disconnected from the piston 3a, as shown in FIGS. 7 and 8, and the shielded contamined needle is discarded.

From the above description, it will be readily apparent to those skilled in the art that the present invention provides a safeguard, not provided heretofore, for medical personnel against exposure to infectious diseases when using catheter-cannula insertion needles.

It is to be understood that the form of the invention herewith shown and described is to be taken as a preferred example of the same, and that various changes in the shape, size and arrangement of parts may be resorted to, without departing from the spirit of the invention or scope of the subjoined claims.

We claim:

1. A disposable, shielded catheter-cannula insertion needle comprising, a housing, a catheter-cannula assembly, means for detachably connecting the catheter-cannula to the distal end of said housing, an insertion needle slidably mounted within said catheter-cannula and having its distal end protruding outwardly from the distal end of said catheter-cannula, a piston assembly slidably mounted within said housing, means for connecting the proximate end of said insertion needle to said piston assembly, a hollow stem having a closed end insertable into the proximate end of said housing, and means for detachably connecting the stem to said piston assembly for drawing the contaminated insertion needle into a shielded position within the housing.

2. A disposable, shielded catheter-cannula insertion needle according to claim 1, wherein the stem is provided with an open end detachably connected to the distal end of said housing to provide a cover for the catheter-cannula and insertion needle before the use thereof.

3. A disposable, shielded catheter-cannula insertion needle according to claim 1, wherein a cap is connected to the distal end of the housing after the catheter-cannula has been removed therefrom, to thereby enclose the contaminated needle in the shielded position within the housing.

4. A disposable, shielded catheter-cannula insertion needle according to claim 1, wherein the means for detachably connecting the catheter-cannula to the distal end of the housing comprises, a base integrally connected to the end of the catheter-cannula, a Luer-lock member, a self-sealing bushing mounted between the base and the Luer-lock member and a sleeve connected between the base and Luer-lock member for holding the base, bushing and Luer-lock member in the assembled position.

5. A disposable, shielded catheter-cannula insertion needle according to claim 1, wherein the means for connecting the proximate end of said insertion needle to said piston assembly comprises a tubular member, one end of said tubular member being connected to the base of the insertion needle, the opposite end of said tubular member being connected to a piston, the interior of said tubular member providing a chamber communicating with the interior of the insertion needle.

6. A disposable, shielded catheter-cannula insertion needle according to claim 5, wherein the housing and tubular member are transparent, whereby the flow of blood into the chamber is readily visible.

7. A disposable, shielded catheter-cannula insertion needle according to claim 1, wherein the means for detachably connecting the stem to said piston assembly comprises, a configured projection on the closed end of said stem, and a correspondingly configured recess formed in the piston assembly for receiving said projection.

8. A disposable, shielded catheter-cannula insertion needle according to claim 1, wherein a spring clip is mounted on the proximate end of said housing to prevent removal of the piston assembly from the housing.

9. A disposable, shielded catheter-cannula insertion needle according to claim 3, wherein the cap and distal end of the housing are provided with cooperating shoulder portions to thereby lock the cap on the housing.

10. A catheter-cannula and insertion needle assembly comprising, a catheter-cannula, a base integrally connected to one end of the catheter-cannula, a Luer-lock member, a selfsealing bushing mounted between the base and the Luer-lock member, a sleeve connected between the base and Luer-lock member for holding the base, bushing and Luer-lock member in an assembled position, and a hollow insertion needle slidably mounted through said self-sealing bushing and said catheter-cannula, to thereby establish a flow passage through said catheter-cannula and said needle, and means for removing said insertion needle from said catheter-cannula and said bushing, whereby the bushing closes upon itself to thereby interrupt the flow passage through the catheter-cannula.

* * * * *